United States Patent
Kim (10) Patent No.: US 11,856,316 B2
(45) Date of Patent: Dec. 26, 2023

(54) METHOD AND APPARATUS FOR CHANGING IMAGE MAGNIFICATION POWER

(71) Applicant: OSSTEMIMPLANT CO., LTD., Seoul (KR)

(72) Inventor: Hye Ra Kim, Incheon (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 0 days.

(21) Appl. No.: 16/757,248

(22) PCT Filed: Oct. 18, 2018

(86) PCT No.: PCT/KR2018/012343
§ 371 (c)(1),
(2) Date: Apr. 17, 2020

(87) PCT Pub. No.: WO2019/078640
PCT Pub. Date: Apr. 25, 2019

(65) Prior Publication Data
US 2021/0195121 A1    Jun. 24, 2021

(30) Foreign Application Priority Data
Oct. 18, 2017    (KR) .................. 10-2017-0135275

(51) Int. Cl.
*G01T 1/29*    (2006.01)
*H04N 5/32*    (2023.01)
(Continued)

(52) U.S. Cl.
CPC ............... *H04N 5/32* (2013.01); *A61B 6/032* (2013.01); *A61B 6/4452* (2013.01); *G01T 1/2985* (2013.01); *A61B 6/14* (2013.01)

(58) Field of Classification Search
CPC ......... A61B 6/032; A61B 6/4452; A61B 6/14; A61B 6/4476; A61B 6/035; A61B 6/08;
(Continued)

(56) References Cited

U.S. PATENT DOCUMENTS 7,347,622 B2 * 3/2008 Sadakane ............... A61B 6/589
378/197
7,688,941 B2 * 3/2010 Thoms ..................... A61B 6/14
378/38
(Continued)

FOREIGN PATENT DOCUMENTS

EP    3037039 A1    6/2016
JP    2006-034670 A    2/2006
(Continued)

OTHER PUBLICATIONS

English Machine Translations of KR20160056986A.*
English Machine Translations of KR20100106879A.*

*Primary Examiner* — David P Porta
*Assistant Examiner* — Djura Malevic
(74) *Attorney, Agent, or Firm* — Bridgeway IP Law Group, PLLC; Sang Ho Lee; Hyun Woo Shin (57) ABSTRACT

Provided is an image capturing method performed by an image capturing apparatus, including acquiring information on first positions which are current positions of a sensor and a generator, moving the sensor and the generator to second positions which are positions at which an image having a magnification power different from a magnification power of an image of an object acquired when the sensor and the generator are located at the first positions is acquired, and acquiring an image of the object, wherein the sensor and the generator move the same distance so that a distance between the sensor and the generator is not changed.

20 Claims, 5 Drawing Sheets

(51) Int. Cl.
*A61B 6/03* (2006.01)
*A61B 6/00* (2006.01)
*A61B 6/14* (2006.01)

(58) Field of Classification Search
CPC ....... A61B 6/4441; A61B 6/469; A61B 6/501; A61B 6/545; A61B 6/588; A61B 6/589; A61B 6/547; A61B 6/4208; G01T 1/2985; H04N 5/32
See application file for complete search history.

(56) References Cited

U.S. PATENT DOCUMENTS

| | | | | |
|---|---|---|---|---|
| 8,144,829 B2* | 3/2012 | Zhu | .................. | A61B 6/542 378/7 |
| 8,300,762 B2* | 10/2012 | Suzuki | .................. | A61B 6/587 378/39 |
| 8,306,181 B2* | 11/2012 | Spartiotis | .................. | A61B 6/14 378/4 |
| 9,060,716 B2* | 6/2015 | Bianconi | .................. | A61B 6/501 |
| 9,265,469 B2* | 2/2016 | Baldini | .................. | A61B 6/14 |
| 9,532,755 B2* | 1/2017 | Choi | .................. | A61B 6/032 |
| 10,172,571 B2* | 1/2019 | Park | .................. | A61B 5/0035 |
| 10,874,360 B2* | 12/2020 | Nishimura | .................. | A61B 6/542 |
| 11,058,379 B2* | 7/2021 | Suuronen | .................. | A61B 6/0407 |
| 2003/0147504 A1 | 8/2003 | Hanover | | |
| 2005/0084147 A1 | 4/2005 | Groszmann | | |
| 2007/0041491 A1* | 2/2007 | Sadakane | .................. | A61B 6/589 378/15 |
| 2008/0299511 A1* | 12/2008 | Thoms | .................. | A61B 6/08 433/68 |
| 2009/0232275 A1* | 9/2009 | Spartiotis | .................. | A61B 6/4441 378/40 |
| 2010/0034340 A1* | 2/2010 | Spartiotis | .................. | A61B 6/588 378/4 |
| 2011/0064188 A1* | 3/2011 | Suzuki | .................. | A61B 6/14 378/62 |
| 2011/0150185 A1* | 6/2011 | Uzbelger Feldman | .................. | A61B 6/145 378/191 |
| 2012/0039436 A1* | 2/2012 | Bothorel | .................. | A61B 6/14 378/11 |
| 2012/0307960 A1* | 12/2012 | Choi | .................. | A61B 6/032 378/4 |
| 2012/0321035 A1* | 12/2012 | Muller | .................. | A61B 6/14 378/4 |
| 2015/0004558 A1* | 1/2015 | Inglese | .................. | A61B 6/4233 433/29 |
| 2015/0010126 A1* | 1/2015 | Rotondo | .................. | A61B 6/032 378/19 |
| 2015/0018622 A1* | 1/2015 | Tesar | .................. | A61B 90/20 600/202 |
| 2016/0345916 A1* | 12/2016 | Lim | .................. | A61B 6/14 |
| 2017/0188981 A1* | 7/2017 | Park | .................. | A61B 6/5247 |
| 2018/0310898 A1* | 11/2018 | Ahn | .................. | A61B 6/00 |
| 2019/0307415 A1* | 10/2019 | Antikainen | .................. | A61B 6/04 |
| 2020/0008760 A1* | 1/2020 | Nishimura | .................. | A61B 6/4435 |
| 2020/0121267 A1* | 4/2020 | Deutschmann | .................. | A61B 6/105 |
| 2020/0315555 A1* | 10/2020 | Sugihara | .................. | A61B 6/14 |
| 2021/0093282 A1* | 4/2021 | Sadakane | .................. | A61B 6/4476 |

FOREIGN PATENT DOCUMENTS

| | | |
|---|---|---|
| KR | 10-2007-0017670 A | 2/2007 |
| KR | 10-2007-0054658 A | 5/2007 |
| KR | 10-2010-0106879 A | 10/2010 |
| KR | 10-2016-0056986 A | 5/2016 |
| KR | 10-2016-0061998 A | 6/2016 |
| WO | 2008/028988 A1 | 3/2008 |

* cited by examiner

METHOD AND APPARATUS FOR CHANGING IMAGE MAGNIFICATION POWER

TECHNICAL FIELD

The present disclosure relates to a method and apparatus of capturing an image, while changing an image magnification power. More particularly, the present disclosure relates to a method and apparatus of changing a magnification power of an X-ray imaging apparatus according to an object.

BACKGROUND ART

An X-ray imaging apparatus widely used in the field of medical technology irradiates a human body with X-rays to acquire an image of an inside of the human body, through which abnormalities in the human body are detected.

A principle of the X-ray imaging apparatus is to irradiate an object with X-rays generated by a generator that generates the X-rays and to receive the X-rays that reach a sensor facing the generator after being partially transmitted or not transmitted through the object. Thereafter, the X-ray imaging apparatus converts the received X-rays to generate an image.

Recently, techniques for the X-ray imaging apparatus that may be used for the purpose of panoramic imaging or computed tomography (CT) imaging as necessary have been disclosed. Related Art document 1 (Korean Patent Laid-Open Publication No. 10-2007-0017670) discloses a technique for performing two functions of panoramic imaging and CT imaging using one device. According to the Related Art document, a technique of separately adopting a sensor for panoramic imaging and a sensor for CT imaging and switching an imaging mode by detachably attaching the sensors as necessary is disclosed.

However, these techniques involve an inconvenience of detachably attaching the sensors each time the imaging mode is switched for panoramic imaging or CT imaging. In addition, in order to acquire an enlarged image of a specific region, separate post-processing is required after image capturing.

In addition, Related Art document 2 (Korean Patent Publication No. 10-2016-0056986) proposes capturing images in various modes by rotating or moving a sensor and a generator of an X-ray imaging apparatus in a longitudinal direction, but there is no specific consideration of a size of a region of interest (ROI) to be actually imaged and a magnification power, and there is a difficulty in implementing a plurality of modes with one sensor without considering an active region within a limited size of the sensor.

DISCLOSURE

Technical Problem

An aspect of the present disclosure provides a method of acquiring a magnified image of a specific portion of a target to be imaged (or an object) with high resolution at a time of capturing an image, without additional post-image processing on the captured image.

Technical Solution

The present disclosure provides an image capturing method performed by an image capturing apparatus, including: acquiring information on first positions which are current positions of a sensor and a generator; moving the sensor and the generator to second positions which are positions at which an image having a magnification power different from a magnification power of an image of an object acquired when the sensor and the generator are located at the first positions is acquired; and acquiring an image of the object, wherein the sensor and the generator move the same distance so that a distance between the sensor and the generator is not changed.

The present disclosure also provides an image capturing apparatus including: a sensor; a generator; and a processor configured to acquire information on first positions which are current positions of the sensor and the generator, to move the sensor and the generator to second positions which are positions at which an image having a magnification power different from a magnification power of an image of an object acquired when the sensor and the generator are located at the first positions is acquired, and control operations of the sensor and the generator to acquire an image of the object, wherein the sensor and the generator move the same distance so that a distance between the sensor and the generator is not changed.

The present disclosure also provides a computer-readable recording medium having a computer program recorded thereon to perform the foregoing image capturing method.

The present disclosure also provides an image capturing system including: the foregoing image capturing apparatus; and a database configured to store the image captured by the image capturing apparatus together with information of the object, wherein the database stores an image of the object at second positions having a magnification power different from a magnification power of the object at first positions.

Advantageous Effects

Using the image processing method and apparatus according to an embodiment, a magnified image of a specific portion of an object may be acquired with high resolution at a time of capturing an image, without separate post-image processing on the captured image.

In addition, using the image processing method and apparatus according to an embodiment, a user may capture a high-resolution magnified image of a specific area of a subject using a normal radiation dose, and thus, unnecessary exposure of the subject to radiation may be reduced.

DESCRIPTION OF DRAWINGS

A detailed description of each drawing is provided to more fully understand the drawings, which are incorporated in the detailed description of the disclosure.

BEST MODES

While a specific structural or functional description with respect to embodiments according to the present disclosure disclosed in this specification is merely provided for the purpose of describing the embodiments of the present disclosure, there are various modifications capable of replacing the embodiments, and the present disclosure is not limited to the embodiments described in this specification.

While the embodiments according to the present disclosure is susceptible to various modifications and alternative forms, specific embodiments thereof are shown by way of examples in the drawings and will herein be described in detail. It should be understood, however, that there is no intent to limit the present disclosure to the particular forms disclosed, but on the contrary, the present disclosure is to cover all modifications, equivalents, and alternatives falling within the spirit and scope of the disclosure.

It will be understood that, although the terms "first," "second," etc. may be used herein to describe various elements, these elements should not be limited by these terms. These terms are only used to distinguish one element from another. For example, a first element could be termed a second element, and, similarly, a second element could be termed a first element, without departing from the scope of the disclosure.

It will be understood that when an element is referred to as being "connected" or "coupled" to another element, it can be directly connected or coupled to the other element or intervening elements may be present. In contrast, it will be understood that when an element is referred to as being "directly connected" or "directly coupled" to another element, there are no intervening elements present. Other expressions describing a relation between elements, that is, "between" and "directly between", or "adjacent to" and "directly adjacent to", etc. should be similarly understood.

The terminology used herein is for the purpose of describing particular embodiments only and is not intended to be limiting of the invention. As used herein, the singular forms "a", "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms used herein including the technical or scientific terms have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

An embodiment of the present disclosure provides an image capturing method of capturing an image of a subject to be imaged at different magnification powers. First, terms for explaining the present disclosure and a basic configuration of the image capturing apparatus will be described with reference to FIGS. 1 and 2.

Figure 1:
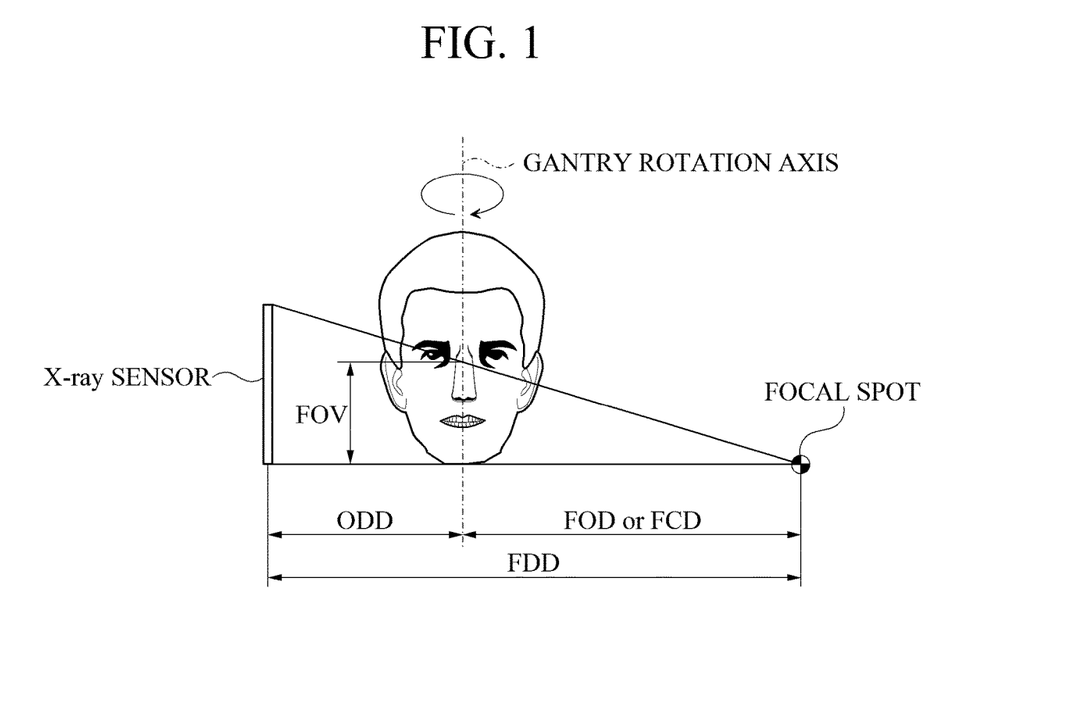
FIG. 1 is a reference drawing illustrating terms used in the present disclosure.

FIG. 1 is a reference drawing for explaining the terms used in the present disclosure. Focal spot to detector distance (FDD) refers to a spatial distance from a generator (focal spot) to a sensor (detector). Focal spot to object distance (FOD) refers to a spatial distance from the generator to an object (to be imaged).

Focal spot to rotation center distance (FCD) refers to a spatial distance from the generator to a rotation axis of a gantry. The rotation axis of the gantry refers to an axis of rotation of the generator and the sensor. Object to detector distance refers to a spatial distance from the object to the sensor. A magnification power described below refers to a value acquired by dividing FDD by FOD.

Field of view (FOV) refers to a size of a region that may be imaged at a time by the sensor, which may be represented by an angle and correspond to a region of interest (ROI) in the present disclosure.

Figure 2:
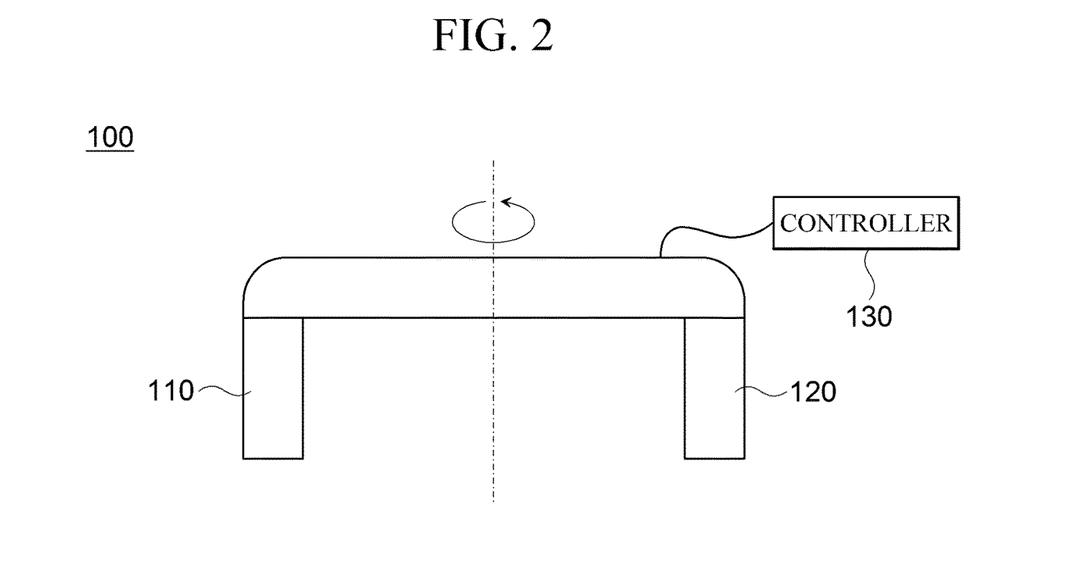
FIG. 2 is a diagram illustrating an image capturing apparatus according to an embodiment.

FIG. 2 is a diagram illustrating an image capturing apparatus 100 according to an embodiment. The image capturing apparatus 100 according to the embodiment includes a generator 110, a sensor 120, and a controller 130.

In an embodiment, the generator 110 may generate X-rays. In an embodiment, the generator 110 generates X-rays according to a first mode or a second mode.

In an embodiment, the mode classifies an image capturing method using X-rays. In an embodiment, the first mode may be a computed tomography (CT) imaging mode. A three-dimensional (3D) structure inside a human body may be recognized by capturing a 3D image through a CT image.

The second mode may be a panoramic image capturing mode. An overall teeth condition and structure may be recognized through a panoramic image and used for a diagnosis and a surgical procedure.

In an embodiment, the generator 110 determines strength, dose, and the like of an X-ray generated according to an imaging mode and irradiated to the sensor 120, and an irradiation range may also be determined through a separate collimator.

In addition, a focus for a specific subject may be differentiated or an X-ray based on other set imaging conditions may be generated.

In an embodiment, the sensor 120 collects X-rays generated by the generator 110. In detail, the sensor 120 absorbs the X-rays generated by the generator 110 and transmitted through a subject according to the first mode or the second mode and converts the X-rays into an electrical signal. An image may be generated using the converted electrical signal.

In addition, in an embodiment, the sensor 120 may change an active region according to each imaging mode. For example, in the first mode and the second mode, X-rays generated by the same generator 110 may be collected but an image may be generated using only X-rays collected through different active regions.

In an embodiment, the controller 130 may configure an imaging environment based on the imaging mode by controlling the imaging conditions or the active region described above in software. In addition, the controller 130 may control physical operations of the generator 110 and the sensor 120 described above by hardware control to configure the imaging environment according to each imaging mode.

Figure 3:
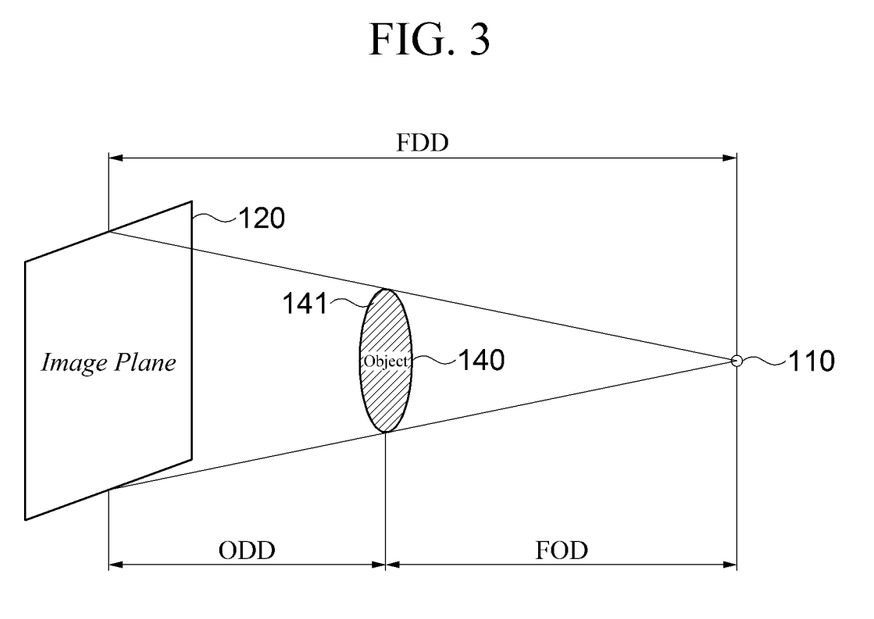
FIGS. 3 and 4 are conceptual views illustrating a method of changing an image magnification power in an image capturing method performed by an image capturing apparatus according to an embodiment.

Hereinafter, a method of changing an image magnification power in an image capturing method performed by the image capturing apparatus 100 according to an embodiment will be described with reference to FIGS. 3 and 4. FIG. 3 is a diagram illustrating positions of the sensor 120, the generator 110, and an object 140, as an object to be imaged, before a magnification power is changed. In FIG. 3, a region of interest (ROI) 141 is set to the entire portion of the object 140.

When X-rays generated by the generator 110 is incident to the sensor 120 after being transmitted through the object 140, a captured image of the object 140 is acquired by the sensor 120. In the example shown in FIG. 3, as the X-rays transmitted through the entire region of the object 140 are incident on an image plane of the sensor 120, the entire region 141 shaded for the object 140 is acquired by the sensor.

Figure 4:
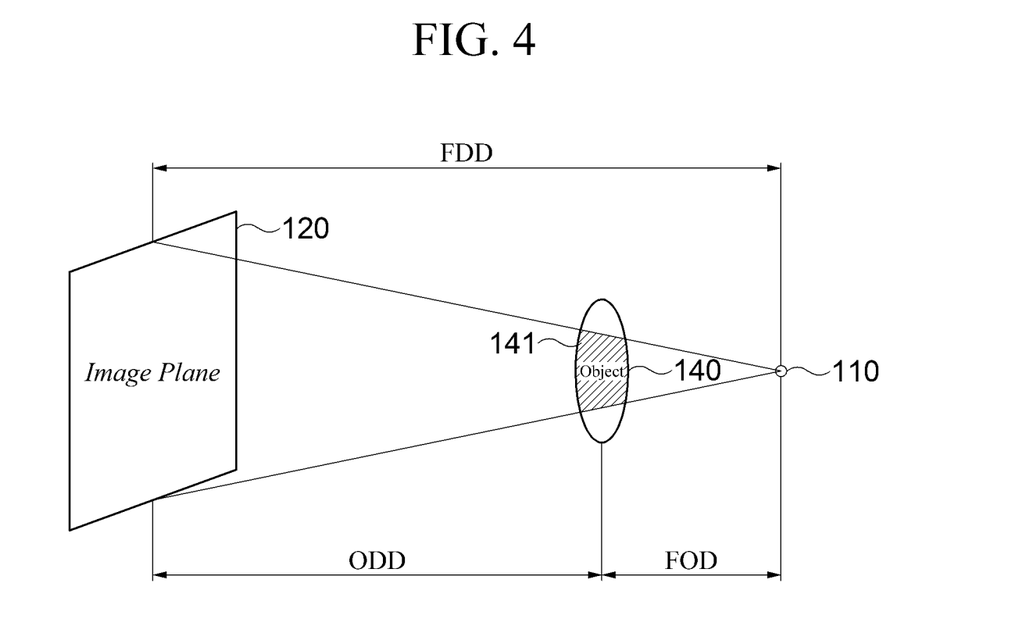

FIG. 4 is a diagram illustrating relative positions of the sensor 120, the generator 110, and the object 140 after a magnification power of the image capturing apparatus 100 according to an embodiment is changed. The image capturing apparatus 100 according to an embodiment moves positions of the sensor 120 and the generator 110 according to an imaging mode. Accordingly, the relative positions of the sensor 120, the generator 110, and the object 140 located therebetween are changed. Here, the sensor 120 and the generator 110 may move the same distance so that the distance between the sensor 120 and the generator 110 does not change. In this case, although the distance between the sensor 120 and the generator 110 is the same, the magnification power may be changed as the distance between the generator 110 and the object 140 changes.

When the relative position of the object 140 in a space between the sensor 120 and the generator 110 is changed, an ODD value is changed as a spatial distance between the sensor 120 and the object 140 is changed and an FOD value is changed as the spatial distance between the generator 110 and the object 140 is changed. However, the sensor 120 and the generator 110 may move the same distance so that the distance between the sensor 120 and the generator 110 does not change. In this case, an FDD value is not changed as the spatial distance between the sensor 120 and the generator 110 is maintained.

For example, as shown in FIG. 4, when the object 140 and the generator 110 are close to each other, the FOD value decreases. However, since the FDD value remains the same, an image captured by magnifying a portion of the object is acquired by the sensor 120. That is, compared with FIG. 3, as X-rays transmitted through a portion of the object 140 are incident on an image plane of the sensor 120, the ROI 141 selected to be shaded in the object 140 in FIG. 4 is acquired as a captured image by the sensor. Accordingly, the image capturing apparatus 100 according to an embodiment may simply acquire the magnified image of the ROI 141 of the object with high resolution without additional software processing.

Positioning of the Sensor 120 and the Generator 110

In an embodiment, the user may determine a relative position of the object 140 located between the sensor 120 and the generator 110 according to an imaging mode to implement a magnification power of an image required for the imaging mode. The imaging mode may include at least one of a panoramic imaging mode and a CT imaging mode.

In addition, if the user wants to capture a magnified image of the specific ROI 141 of the object 140, the image capturing apparatus 100 may move the positions of the sensor 120 and the generator 110 to capture the magnified image.

In an embodiment, the user may determine a relative position of the object 140 located between the sensor 120 and the generator 110 to acquire a maximum magnification power image of the ROI 141 of the object 140 by an active region of the sensor 120. The ROI may be a region of a portion of a mouth of a subject imaged for an X-ray image. For example, the ROI may be an upper jaw (maxilla), a lower jaw (mandible), or a part thereof.

In an embodiment, the positions of the sensor 120 and the generator 110 for capturing an image of the ROI 141 may be determined based on a position and an area of the ROI 141 in the real world coordinate system.

The image capturing apparatus 100 may determine a position of the sensor 120 and the generator 110 to a position where the outermost portion of the ROI 141 in the real world coordinate system is in contact with a path of light incident on the outermost portion of an active region of the sensor 120 from the generator 110 so that the maximum magnification power image may be acquired using the active region of the sensor 120.

An example thereof is shown in FIG. 4. FIG. 4 illustrates an example in which the uppermost and lowermost portions of the ROI 141 are in contact with upper and lower paths of light incident on the outermost portion of the active region (image plane) of the sensor 120 from the generator 110.

In another embodiment, the positions of the sensor 120 and the generator 110 may be determined based on a position and an area of the ROI 141 in the current image acquired at the current positions of the sensor 120 and the generator 110. The image capturing apparatus 100 may calculate a position correction value for converting center coordinates of the ROI 141 into center coordinates of the current image and an area correction value for converting the area of the ROI 141 to the area of the current image and determine positions of the sensor 120 and the generator 110 at which the image of the ROI is maximized using the position correction value and the area correction value.

In another embodiment, if there are a plurality of ROIs in the object 140, the positions of the sensor 120 and the generator 110 may be determined as positions at which the maximum magnification power image including all the plurality of ROIs may be acquired by the active region of the sensor.

In consideration of the fact that the object 140 is an amorphous solid body, the image capturing apparatus 100 may calculate the positions of the sensor 120 and the generator 110 at each angle at which the sensor 120 and the generator 110 rotate. The positions of the sensor 120 and the generator 110 for acquiring the maximum magnification power image of the ROI 141 of the object 140 calculated as described above may be calculated in advance, stored in the memory, and may be loaded to be used as needed later.

In an embodiment, the image capturing apparatus 100 may calculate relative positions of the sensor 120 and the generator 110 regarding the object 140 located between the sensor 120 and the generator 110 in advance in consideration of a size of the sensor 120, a position and a size of the ROI 141 in the object 140, a magnification power, and an FDD value and selectively use the calculated results as necessary. For example, the image capturing apparatus 100 may locate the object 140 spaced apart from the generator 110 than a previously calculated position, at a position at which the entire portion of the ROI 141 is maximally acquired by the sensor 120 so that a phenomenon in which a portion (in particular, the outermost portion) of the ROI 141 set for the object 140 is not acquired by the sensor 120 does not occur.

Movement of Positions of Sensor 120 and Generator 110

The image capturing apparatus 100 may move the positions of the sensor 120 and the generator 110 relative to the object 140, while maintaining the same spatial distance between the sensor 120 and the generator 110. The image capturing apparatus 100 may include a moving unit for moving the sensor 120 and the generator 110, and the moving unit may include an actuator or the like. The moving unit may be directly coupled to the sensor 120 and the generator 110 or may be coupled to an accommodating module that accommodates the sensor 120 and the generator 110.

In an embodiment, in order to efficiently acquire a magnified image, the image capturing apparatus 100 may change 3D positions of the sensor 120 and the generator 110 so that an image of the ROI 141 acquired by the sensor 120 and the generator 110 is a specific portion of the object. To this end, the image capturing apparatus 100 may further include a moving unit for changing the 3D positions of the sensor 120 and the generator 110. Alternatively, the image capturing apparatus 100 may change a 3D position of the object 140 so that the image of the ROI acquired by the sensor 120 and the generator 110 may be a specific portion of the object, and the image capturing apparatus 100 may include a moving unit for moving the object 140.

In an embodiment, the sensor 120 and the generator 110 may each be connected to a gantry through the moving unit. A sensor moving unit and a generator moving unit may horizontally and/or vertically move the sensor 120 and the generator 110 in the gantry. The sensor moving unit and the generator moving unit may horizontally/vertically move the positions of the sensor 120 and the generator 110 along a movable portion of the gantry. The sensor moving unit and the generator moving unit may extend in a horizontal/vertical direction to move the positions of the sensor 120 and the generator 110 horizontally/vertically.

In an embodiment, the sensor 120 and the generator 110 may move to positions at which the center of the sensor 120, the center of the generator 110, and the center of the ROI 141 are aligned to maximally acquire a magnified image of the ROI 141 of the object 140. If necessary, the sensor 120 and the generator 110 may be tilted in order to capture an image in an oblique direction.

In another embodiment, the sensor 120 and the generator 110 may be fixed to the gantry. In the present embodiment, the gantry may be moved to move the fixed sensor 120 and the generator 110. A gantry moving unit may move the gantry horizontally/vertically. Here, a position of a rotation axis of the gantry may not change in the real world coordinate system. In order to implement this, the gantry may be divided into a part forming the rotation axis and a part connecting the sensor 120 and the generator 110, and only the part connecting the sensor 120 and the generator 110 may be moved relative to the part forming the rotation axis of the gantry.

In order to maximally acquire the magnified image of the ROI 141 of the object 140, the gantry may move to the position where the center of the sensor 120 and the center of the generator 110 and the center of the ROI 141 are aligned. If necessary, the gantry may be tilted for imaging in the oblique direction.

As an alternative embodiment, the image capturing apparatus 100 may move the position of the object 140 between the sensor 120 and the generator 110. The image capturing apparatus 100 may include a moving unit for moving the object 140, and the moving unit may be configured as an actuator or the like. The moving unit may be coupled to a module in which the object 140 is located. For example, if the object is a human, the module in which the object 140 is located may be a chair on which a person may sit or a bed in which a person may lie down.

Figure 5:
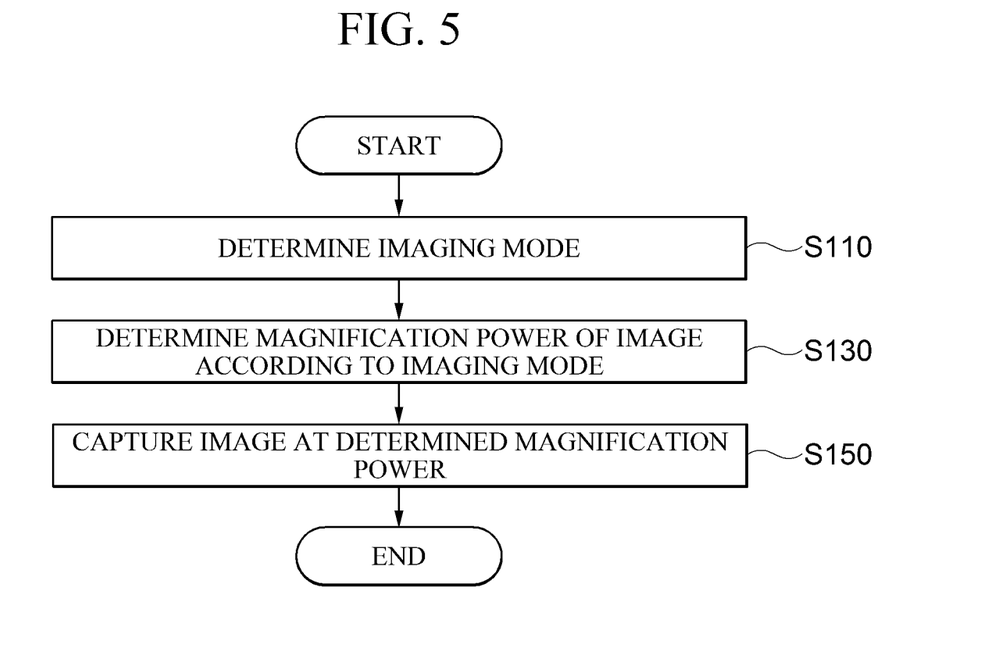
FIG. 5 is a flowchart illustrating an operation of an image capturing apparatus according to an embodiment.

FIG. 5 is a flowchart illustrating an operation of the image capturing apparatus 100 according to an embodiment. First, the image capturing apparatus 100 determines an imaging mode in operation S110. The imaging mode may be previously determined. The imaging mode may be one of a panoramic imaging mode and a CT imaging mode and may further include a separate imaging mode for changing a magnification power for the ROI set according to an embodiment.

The image capturing apparatus 100 may determine an imaging mode according to a user input. Alternatively, the image capturing apparatus 100 may sequentially change the imaging mode in order to acquire an image of an object according to pre-programmed image capturing order.

Next, the image capturing apparatus 100 determines a magnification power of the image according to the selected imaging mode in operation S130. The magnification power according to the imaging mode may be stored in advance in the image capturing apparatus 100. Alternatively, the image capturing apparatus 100 may query the user to select a magnification power and determine the magnification power according to the user input.

Next, the image capturing apparatus 100 captures an image according to the determined magnification power in operation S150. In order to change the magnification power, the image capturing apparatus 100 may change the positions of the sensor 120 and the generator 110 or change the position of the object 140 as described above with reference to FIG. 4.

In an embodiment, a plurality of independent ROIs for the object 140 may be set. In this case, imaging positions of the sensor 120 and the generator 110 for capturing an image at the maximum magnification power may be set for each ROI. A plurality of imaging positions of the sensor 120 and the generator 110 for imaging the ROIs independently are generated.

In order to independently capture an image for each ROI, the sensor 120 and the generator 110 should perform position movement several times. In order to minimize a moving distance of the sensor 120 and the generator 110, the shortest distance path between the sensor 120 and the generator 110 using the plurality of imaging positions as stops may be calculated. Accordingly, a position movement schedule of the sensor 120 and the generator 110 may be generated. The image capturing apparatus 100 may capture images of the ROIs according to the generated position movement schedule.

Figure 6:
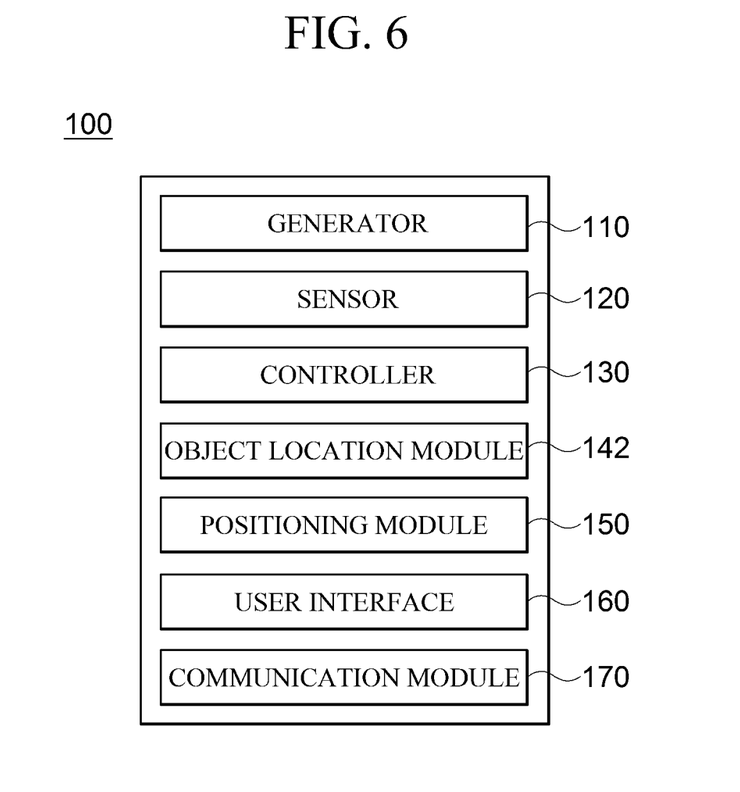
FIG. 6 is a block diagram illustrating a specific configuration of an image capturing apparatus according to an embodiment.

FIG. 6 is a block diagram illustrating a specific configuration of an image capturing apparatus 100 according to an embodiment. As illustrated in FIG. 6, the image capturing apparatus 100 according to an embodiment may include the generator 110, the sensor 120, a controller 130, an object location module 142, a positioning module 150, a user interface 160, and a communication module 170. The object location module 142, the user interface 160, and the communication module 170 may be selectively used and omitted according to an embodiment.

As described above, as the generator 110, an X-ray generator commonly used as a light source for generating X-rays may be adopted and used. If necessary, the generator 110 may further include a collimator.

As the sensor 120, an X-ray sensor generally used to collect X-rays to acquire an image may be adopted and configured as described above. The sensor 120 may be a large area sensor for panoramic or CT imaging. A size of the sensor 120 may be selected in consideration of a size of an ROI in the object 140, a magnification power, and the FDD value.

The controller 130 includes a processor and a memory. The processor controls the image capturing apparatus 100 and performs control to perform the image capturing method described above. The memory includes temporary and non-temporary data necessary for the image capturing apparatus to operate. The memory may include a magnification power of an image and corresponding position data of the generator 110 and the sensor 120 according to an imaging mode.

The object location module 142 accommodates an object, thereby allowing a position of the object to be specified. The object location module 142 may be omitted as an optional component.

The positioning module 150 moves positions of the generator 110 and the sensor 120. According to an embodiment, the positioning module 150 may move a position of the object location module 142.

As the user interface 160, general input device and output device may be adopted as an interface unit between the image capturing apparatus 100 and the user. As the communication module 170, a general wired/wireless communication module may be adopted as an interface unit between the image capturing apparatus 100 and an external device. The user interface 160 and the communication module 170 may be omitted as optional components.

Figure 7:
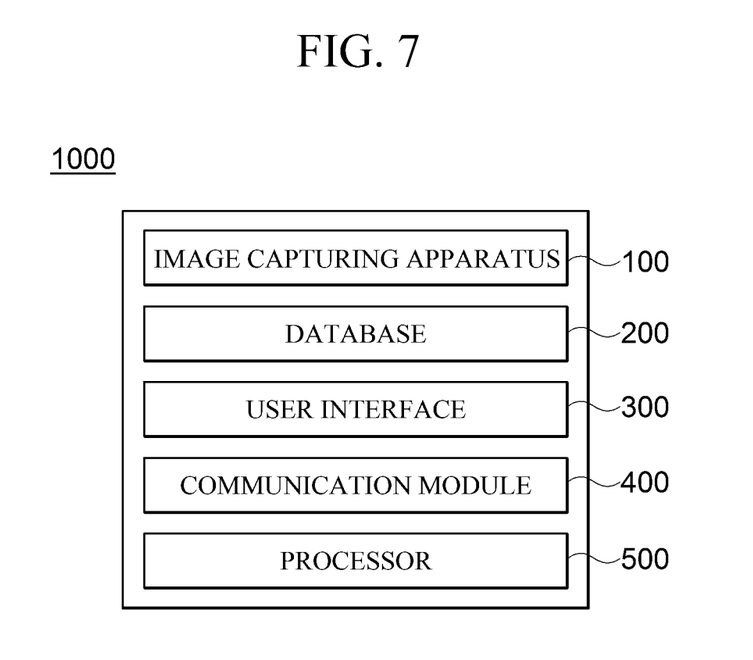
FIG. 7 is a block diagram illustrating a configuration of an image capturing system including an image capturing apparatus according to an embodiment.

FIG. 7 is a block diagram illustrating a configuration of an image capturing system 1000 including the image capturing apparatus 100 according to an embodiment. The image capturing system 1000 according to an embodiment may include the image capturing apparatus 100 of FIG. 6, a database 200, and a processor 500. In addition, the image capturing system 1000 may further include the user interface 300 and the communication module 400.

The image capturing system 1000 may further include the database 200 to store image data of an object acquired from the image capturing apparatus 100 with respect to the object. For example, when used in a hospital, a doctor may store an X-ray image captured for a patient in the database by designating the patient.

The image capturing method according to the embodiments described above may be implemented in a program instruction form that can be performed through various computing means and recorded in computer-readable medium. The computer-readable medium may also include program instructions, data files, data structures, and the like alone or in combination. The program instructions recorded in the medium may be designed and configured specially for the embodiments or be known and available to those skilled in computer software. Examples of computer-readable medium include magnetic medium such as hard disks, floppy disks, and magnetic tape; optical medium such as CD ROM disks and DVDs; magneto-optical medium such as floptical disks; and hardware devices that are specially configured to store and perform program instructions, such as read-only memory (ROM), random access memory (RAM), flash memory, and the like. Examples of program instructions include both machine code, such as produced by a compiler, and higher level code that may be executed by the computer using an interpreter or the like.

The image capturing method according to the embodiments described above may be recorded in non-transitory computer-readable medium including program instructions to implement various operations embodied by a computer. The media may also include, alone or in combination with the program instructions, data files, data structures, and the like. The media and program instructions may be those specially designed and constructed for the purposes, or they may be of the kind well-known and available to those having skill in the computer software arts. Examples of non-transitory computer-readable medium include magnetic media such as hard disks, floppy disks, and magnetic tape; optical media such as CD ROM disks and DVD; magneto-optical media such as floptical disks; and hardware devices that are specially to store and perform program instructions, such as read-only memory (ROM), random access memory (RAM), flash memory, and the like. Examples of program instructions include both machine code, such as produced by a compiler, and files containing higher level code that may be executed by the computer using an interpreter.

Each of the drawings referred to in the foregoing description of the embodiments is merely an embodiment illustrated for convenience of description, and items, contents, and images of information displayed on each screen may be modified and displayed in various forms.

Although embodiments of the present disclosure have been disclosed for illustrative purposes, those skilled in the art will appreciate that various modifications, additions and substitutions are can be made without departing from the scope and spirit of the disclosure as disclosed in the accompanying claims. Therefore, the technical scope of the present disclosure should be defined by the technical spirit and scope of the accompanying claims.

The invention claimed is:

1. An image capturing method performed by an image capturing apparatus, the image capturing method comprising:
   acquiring information on first positions which are current positions of a sensor and a generator, the first positions corresponding to a first imaging mode;
   entering a second image mode different from the first imaging mode;
   according to the entering the second image mode, moving the sensor and the generator to second positions which are positions at which an image having a magnification power different from a magnification power of an image of an object acquired when the sensor and the generator are located at the first positions is acquired, the second positions corresponding to the second imaging mode; and
   performing the second imaging mode to acquire an image of the object,
   wherein the sensor and the generator move the same distance so that a distance between the sensor and the generator is not changed at the first positions and the second positions,
   wherein a distance between the generator and the object at the first positions is different from a distance between the generator and the object at the second positions,
   wherein the images acquired respectively at the first positions and the second positions are acquired by the identical sensor, and
   wherein the first positions and the second positions are determined according to an imaging mode for the object, and the imaging mode includes at least one of a panoramic imaging mode and a computed tomography (CT) imaging mode.

2. The image capturing method of claim 1, wherein the sensor is one large area sensor for panoramic or computed tomography (CT) imaging.

3. The image capturing method of claim 1, wherein the second positions are determined as positions at which a maximum magnification power image of a region of interest (ROI) of the object is acquired by an active region of the sensor without separate post-image processing, and the ROI includes a portion of a mouth of the object.

4. The image capturing method of claim 3, wherein the second positions are determined based on a position and area of the ROI in a real world coordinate system or a position and area of the ROI in the image acquired by the sensor and the generator located at the first positions.

5. The image capturing method of claim 3, wherein the second positions are determined as positions at which a maximum magnification power image including all of a plurality of ROIs can be acquired by the active region of the sensor, when there are a plurality of ROIs in the object.

6. The image capturing method of claim 3, wherein the sensor and the generator move to a position at which the center of the sensor, the center of the generator, and the center of the ROI are aligned.

7. The image capturing method of claim 3, wherein the sensor and the generator rotate with the object interposed therebetween, and the second positions are calculated at every rotation angle of the sensor and the generator.

8. The image capturing method of claim 3, wherein the second positions are previously determined at every ROI of the object and stored in a memory.

9. The image capturing method of claim 1, wherein a plurality of ROIs of the object exist,
the second positions are determined at each of the plurality of ROIs, wherein the second positions are positions at which a maximum magnification power image of the ROIs of the object can be acquired based on a position and area of the ROIs of the object,
a movement schedule of the sensor and the generator are generated according to the plurality of second positions such that movement of the sensor and the generator is minimized, and
the sensor and the generator move according to the generated schedule.

10. A non-transitory computer-readable recording medium having a computer program recorded thereon to perform the method of claim 1.

11. The image capturing method of claim 3, wherein an uppermost and lowermost portions of the ROI are in contact with upper and lower paths of light incident on an outermost portion of the active region of the sensor from the generator.

12. An image capturing apparatus comprising:
a sensor;
a generator; and
a processor configured to:
acquire information on first positions which are current positions of the sensor and the generator, the first positions corresponding to a first imaging mode;
enter a second imaging mode different from the first imaging mode;
move the sensor and the generator to second positions which are positions at which an image having a magnification power different from a magnification power of an image of an object acquired when the sensor and the generator are located at the first positions is acquired, the second positions corresponding to the second imaging mode; and
control operations of the sensor and the generator to perform the second imaging mode for acquiring an image of the object,
wherein the sensor and the generator move the same distance so that a distance between the sensor and the generator is not changed at the first positions and the second positions,
wherein a distance between the generator and the object at the first positions is different from a distance between the generator and the object at the second positions,
wherein the images acquired respectively at the first positions and the second positions are acquired by the identical sensor, and
wherein the first positions and the second positions are determined according to an imaging mode for the object, and the imaging mode includes at least one of a panoramic imaging mode and a computed tomography (CT) imaging mode.

13. The imaging capturing apparatus of claim 12, wherein the sensor and the generator are each connected to a gantry, and
the sensor and the generator horizontally or vertically move in the gantry to move to the second positions.

14. The imaging capturing apparatus of claim 12, wherein the sensor and the generator are each connected to the gantry,
the gantry vertically or horizontally move to move positions of the sensor and the generator, and
a position of a rotation axis of the gantry does not change in a real world coordinate system.

15. The imaging capturing apparatus of claim 12, wherein the sensor is one large area sensor for panoramic or CT imaging.

16. The image capturing apparatus of claim 12, wherein the second positions are determined as positions at which a maximum magnification power image of a ROI of the object is acquired by an active region of the sensor without separate post-image processing, and
the ROI includes a portion of a mouth of the object.

17. The image capturing apparatus of claim 16, wherein an uppermost and lowermost portions of the ROI are in contact with upper and lower paths of light incident on an outermost portion of the active region of the sensor from the generator.

18. The image capturing apparatus of claim 12, wherein the second positions are positions at which the center of the sensor, the center of the generator, and the center of the ROI are aligned.

19. The image capturing apparatus of claim 18, wherein the sensor and the generator are moved according to movement of a gantry to which the sensor and the generator are connected, and
the gantry is tilted so that the sensor and the generator are located at a position at which the second positions are positions at which the center of the sensor, the center of the generator, and the center of the ROI are aligned.

20. An image capturing system comprising:
the image capturing apparatus of claim 12; and
a database configured to store the image captured by the image capturing apparatus together with information of the object,
wherein the database stores the image of the object.

* * * * *